(12) United States Patent
Omonira et al.

(10) Patent No.: US 10,890,424 B2
(45) Date of Patent: Jan. 12, 2021

(54) BIOCOMPATIBLE AMMUNITION

(71) Applicant: LAZARUS SOLUTIONS LLC, Katy, TX (US)

(72) Inventors: Benjamin Omonira, Katy, TX (US); Jonathan Omonira, Katy, TX (US); Elise Hackney, Katy, TX (US); Nathank Panak, Katy, TX (US); Seth Reine, Katy, TX (US)

(73) Assignee: LAZARUS SOLUTIONS, LLC, Katy, TX (US)

( * ) Notice: Subject to any disclaimer, the term of this patent is extended or adjusted under 35 U.S.C. 154(b) by 0 days.

(21) Appl. No.: 16/702,071

(22) Filed: Dec. 3, 2019

(65) Prior Publication Data

US 2020/0109928 A1     Apr. 9, 2020

Related U.S. Application Data

(63) Continuation-in-part of application No. 15/871,697, filed on Jan. 15, 2018, now Pat. No. 10,495,429.

(60) Provisional application No. 62/446,442, filed on Jan. 15, 2017.

(51) Int. Cl.
| | |
|---|---|
| *F42B 12/54* | (2006.01) |
| *A61K 9/16* | (2006.01) |
| *A61K 33/06* | (2006.01) |
| *F42B 12/40* | (2006.01) |

(52) U.S. Cl.
CPC ............ *F42B 12/54* (2013.01); *A61K 9/1629* (2013.01); *A61K 33/06* (2013.01); *F42B 12/40* (2013.01)

(58) Field of Classification Search
CPC ........................................................ F42B 12/54
USPC ........................................................ 102/512
See application file for complete search history.

(56) References Cited

U.S. PATENT DOCUMENTS 8,997,653 B1 *  4/2015  Calvert ..................... F42B 5/02
                                                                 102/439
2016/0298947 A1 * 10/2016  Rubin ..................... F42B 12/54

* cited by examiner

*Primary Examiner* — Reginald S Tillman, Jr.
(74) *Attorney, Agent, or Firm* — Mangum IP, LLC (57) ABSTRACT

The disclosure describes, in various example embodiments, a small arms or firearm projectile including a shell and a hemostatic material retained within the shell. The hemostatic material has a mechanical modulus above 25,000 Pa. In some embodiments, the shell includes a plurality of perforations. In some embodiments, the plurality of perforations are configured to provide, upon an impact of the projectile, fluid communication between the hemostatic material and the exterior of the shell via the plurality of perforations. In some embodiments, the hemostatic material includes a polymer core configured to provide a scaffold for inducing hemostasis in a local wound volume. In some embodiments, the projectile includes a contrasting agent. In some embodiments, the projectile includes a lubricating agent retained in the interior of the shell. In some embodiments, the projectile further includes 0.5 to 3 grains of Kaolin retained in the interior of the shell.

18 Claims, 10 Drawing Sheets

BIOCOMPATIBLE AMMUNITION

CROSS-REFERENCE TO RELATED APPLICATIONS

This application is a continuation-in-part of U.S. patent application Ser. No. 15/871,697 which was filed Jan. 15, 2018, which claims the benefit of U.S. Provisional Application No. 62/446,442 which was filed Jan. 15, 2017, both of which are fully incorporated herein by reference.

BACKGROUND

The present disclosure relates to less-lethal and less-than-lethal ammunition. More specifically, the present disclosure relates to small arms or firearm projectiles carrying non-traditional payloads.

SUMMARY

The disclosure describes, in various example embodiments, a small arms or firearm projectile including a shell and a hemostatic material retained within the shell. The hemostatic material has a mechanical modulus above 25,000 Pa. In some embodiments, the shell includes a plurality of perforations. In some embodiments, the plurality of perforations are configured to provide, upon an impact of the projectile, fluid communication between the hemostatic material and the exterior of the shell via the plurality of perforations. In some embodiments, the hemostatic material includes a polymer core configured to provide a scaffold for inducing hemostasis in a local wound volume. In some embodiments, the projectile includes a contrasting agent. In some embodiments, the projectile includes a lubricating agent retained in the interior of the shell. In some embodiments, the projectile further includes 0.5 to 3 grains of Kaolin retained in the interior of the shell. In some embodiments, the hemostatic material is includes a plurality of expandable polymer pellets. In some embodiments, the projectile includes a disinfecting agent retained in the interior of the shell. In some embodiments, the projectile has a jacket with a thickness between 0.01 inches and 0.015 inches and the length of the projectile is between 0.6 inches and 0.75 inches. In some embodiments, the projectile the shell has a front, a back, and a weighted pellet bonded to the back of the shell.

A small arms or firearm cartridge is disclosed. The cartridge includes a cartridge case having an open end, a closed end, and a longitudinal axis. The cartridge includes a shell having an interior and an exterior. The shell is configured for secure retention in the open end of the cartridge case. The cartridge includes a propellant retained within the cartridge case between the shell and the closed end of the cartridge case. The cartridge includes an enclosed material retained in the interior of the shell. The enclosed material is configured as a hemostatic material. The hemostatic material has a mechanical modulus above 25,000 Pa. In some embodiments, the shell includes a plurality of perforations, and the plurality of perforations are configured to provide, upon an impact of the cartridge, fluid communication between the hemostatic material and the exterior of the shell via the plurality of perforations. In some embodiments, the hemostatic material includes a polymer core configured to provide a scaffold for inducing hemostasis in a local wound volume. In some embodiments, the cartridge includes a contrasting agent. In some embodiments, the cartridge includes a lubricating agent retained in the interior of the shell. In some embodiments, the cartridge includes 0.5 to 3 grains of Kaolin retained in the interior of the shell. In some embodiments, the hemostatic material is comprised of a plurality of expandable polymer pellets. In some embodiments, the cartridge includes a disinfecting agent retained in the interior of the shell. In some embodiments, the cartridge includes a jacket with a thickness between 0.01 inches and 0.015 inches a length between 0.6 inches and 0.75 inches. In some embodiments, the shell has a front, a back, and a weighted pellet bonded to the back of the shell.

Other aspects of the disclosure will become apparent by consideration of the detailed description and accompanying drawings.

DETAILED DESCRIPTION

This disclosure is not limited in its application to the details of construction and the arrangement of components set forth in the following example descriptions or illustrated in the following drawings. The disclosure is capable of other embodiments and of being practiced or of being carried out in various ways, as one of ordinary skill in the art would understand.

Figure 1:
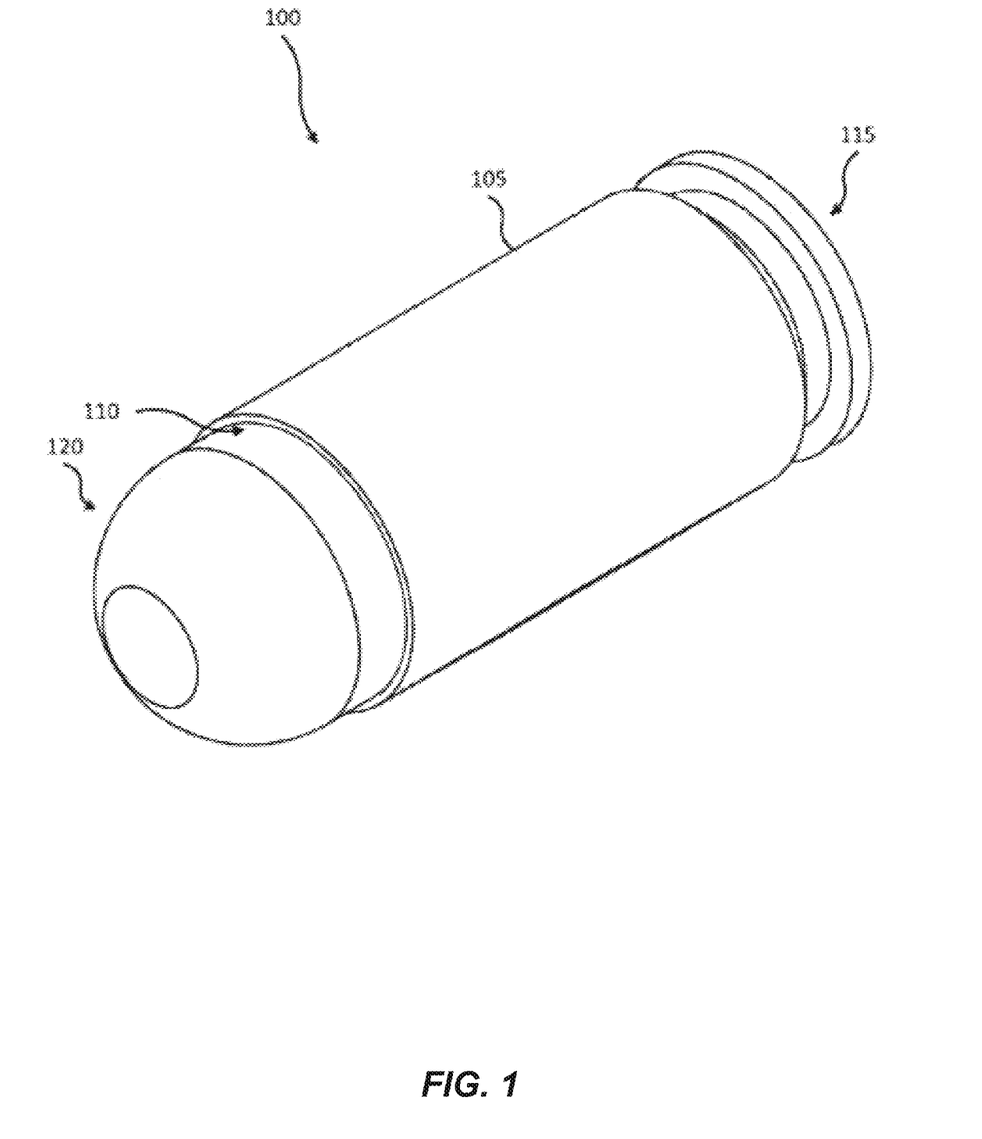
FIG. 1 is a perspective view of a small arms or firearm cartridge, according to some embodiments.

FIG. 1 illustrates a perspective view of a small arms or firearm cartridge 100, such as a handgun or rifle cartridge. The cartridge 100 includes a shell casing 105 having a forward opening 110 and a heel 115. The cartridge 100 further includes a projectile 120 retained in the forward opening 110. In some embodiments, the projectile 120 may be retained in the forward opening 110 with a crimp fit, interference fit, or any other suitable retention method. The cartridge 100 further includes a primer in the heel 115 and a propellant between the primer and the projectile 120.

Figure 2:
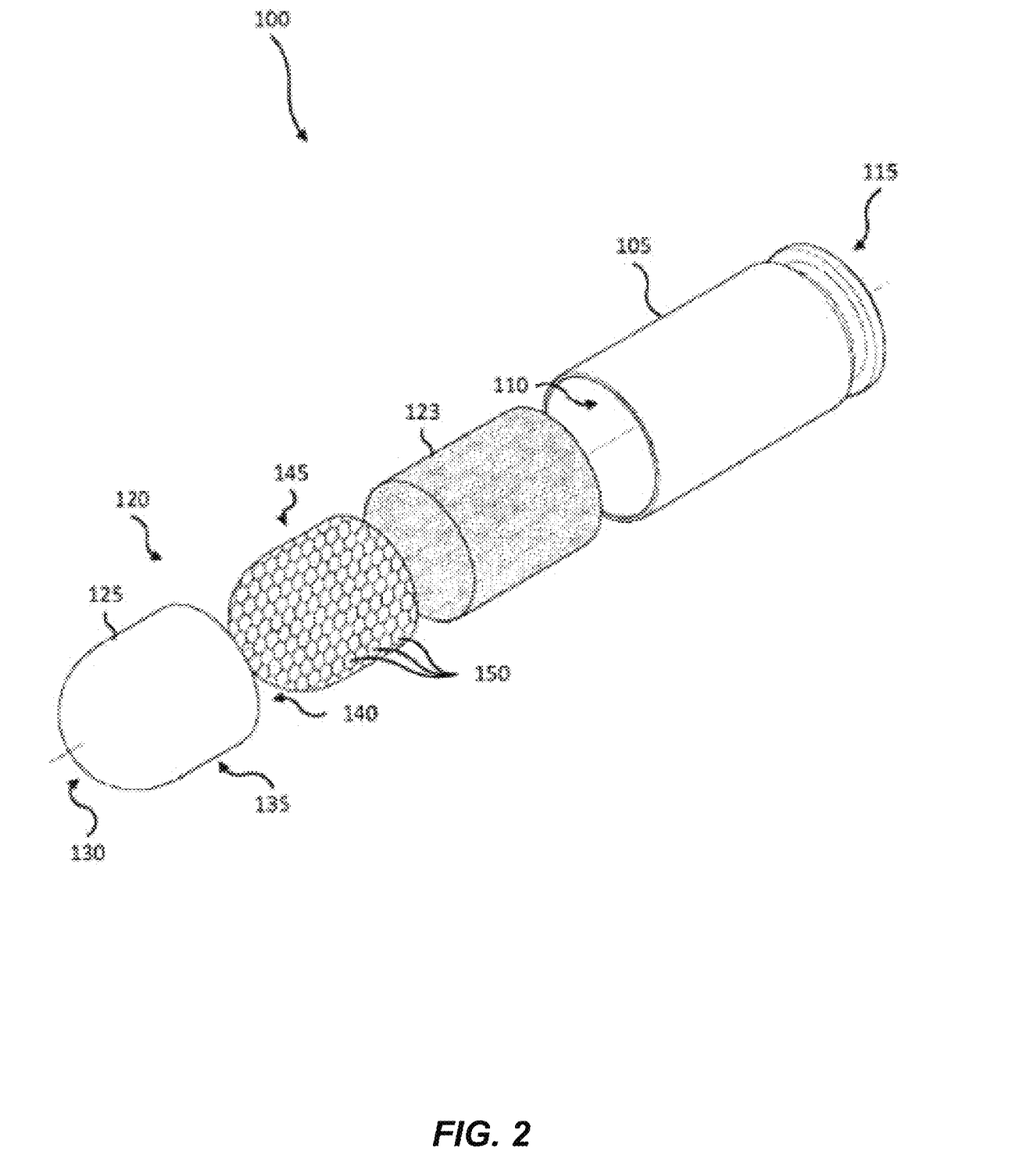
FIG. 2 is an exploded perspective view of a small arms or firearm cartridge including a hemostatic material retained within a bullet jacket, according to some embodiments.

FIG. 2 illustrates an exploded perspective of the cartridge 100. The cartridge includes a propellant 123 behind the projectile 120. The projectile 120 includes a jacket 125 having a tip portion 130, an elongate body portion 135, and a tail portion 140. Additionally, the projectile 120 includes a hollow interior enclosed by the tip portion 130, the body portion 135, and the tail portion 140. The hollow interior is generally indicated by the interior boundary volume 145. The interior boundary volume 145 is filled with a hemostatic material 150. In some embodiments, the hemostatic material 150 includes a factor concentrator. This class of hemostatic material 150 works through fast absorption of the water content of blood; consequently, concentration of its cellular and protein components results in clot formation. Accordingly, factor concentrators decrease lethality at a wound or delivery site. One example of a factor concentrator is granular mineral zeolite, which is composed of oxides of silicon, sodium, aluminum, magnesium, as well as trace amounts of quartz. The granular mineral zeolite acts as a molecular sieve and rapidly absorbs water through physical reactions.

In some embodiments, the jacket 125 has a thickness between 0.01 inches and 0.015 inches. In some embodiments, the jacket 125 is configured to reduce fragmentation upon impact. In some embodiments, the projectile 120 has a length between 0.6 and 0.75 inches.

In some embodiments, the hemostatic material 150 includes a mucoadhesive agent. These agents act through a strong adherence to the living tissue, and physically block bleeding from a delivery site. Chitosan granules, a mucoadhesive agent, or its lyophilized derivatives, promote clot formation through adsorption and dehydration, and the advancement of red blood cell bonding. In some embodiments, the chitosan may further be combined with silica and/or polyethylene, which form a structure of a dressing at the delivery site.

In some embodiments, the hemostatic material 150 is a self-expanding hemostatic polymer or, for example, a shape memory polymer foam. In some embodiments, the hemostatic material 150 is configured to expand on contact with a liquid. In some embodiments hemostatic material 150 is configured to expand to at least two times the initial volume. In some embodiments hemostatic material 150 is configured to expand to at least four times the initial volume. In some embodiments hemostatic material 150 is configured to expand to at least six times the initial volume. In some embodiments hemostatic material 150 is configured to expand to at least eight times the initial volume. In some embodiments hemostatic material 150 is configured to expand to at least ten times the initial volume. In some embodiments, the hemostatic material is configured to expand to 80% or greater of its maximum expansion capacity within 30 seconds of impact. In some embodiments, the hemostatic material is configured to expand to 80% or greater of its maximum expansion capacity within one minute of impact. In some embodiments, the hemostatic material is configured to expand to 80% or greater of its maximum expansion capacity within two minutes of impact. In some embodiments, the hemostatic material 150 is a plurality of self-expanding hemostatic polymer pellets. In some embodiments, the hemostatic material 150 includes smectite granules. In some embodiments, the hemostatic material 150 includes procoagulant supplementors, such as a dry fibrin sealant dressing. In some embodiments, the hemostatic material 150 may be a combination of one or more of the aforementioned materials. In some embodiments, the hemostatic material may have a mechanical modulus of greater than 25,000 Pa. This allows the hemostatic material to expand against internal organs and tissues.

In some embodiments, the hemostatic material 150 includes Kaolin. In some embodiments, the expandable polymer is impregnated, coated, or bonded with Kaolin. In some embodiments, the hemostatic material contains 0.5 to 3 grains of Kaolin. In some embodiments, the hemostatic material contains 1 to 3 grains of Kaolin. In some embodiments, the hemostatic material contains 1.5 to 2.5 grains of Kaolin.

In some embodiments, the hemostatic material 150 includes a polymer core configured to provide a scaffold for inducing hemostasis in the local wound volume. In some embodiments, the polymer core is sized to prevent solid polymers from leaving the local wound volume through microtears, veins, or arteries near the wound. Exemplary polymer core structures may include pellets, meshes, gauzes, fabrics, nonwoven fabrics, melt-blown webs, spun-bonded webs, thermal-bonded webs, spun-laced webs, undercast padding, and/or shape-memory structures.

In some embodiments, the interior boundary volume 145 contains a lubricating agent. In some embodiments, the lubricating agent serves the purpose of reducing friction between portions of the hemostatic material 150 in order to allow for better separation within the wound cavity. In some embodiments, the lubricating agent is a dry lubricant, such as graphite. In some embodiments, hemostatic agents with low coefficients of friction serve as dry lubricating agents. In some embodiments, the lubricating agent is Kaolin.

In some embodiments, the interior boundary volume 145 contains a disinfecting agent. In some embodiments, the disinfecting agent includes medical disinfectants. In some embodiments, the disinfecting agent includes broad-spectrum antibiotics. In some embodiments, the disinfecting agent is configured to reduce risk of infection to the gun owner or first responders resulting from exposure to the target's blood.

In some embodiments, the interior boundary volume 145 contains a cauterizing agent. In some embodiments, the cauterizing agent includes a zeolite material. In some embodiments, the cauterizing agent is configured to reduce blood loss of the target. In some embodiments, the cauterizing agent is configured to reduce exposure of the gun owner or first responders to the target's blood.

In some embodiments, portions of the projectile 120, which can include—but are not limited to—the jacket 125, the tip portion 130, the elongate body portion 135, the tail portion 140, and the hemostatic agent 150, can be coated with, bonded to, or impregnated with a contrasting agent. In some embodiments, the contrasting agent can include barium sulfate. In some embodiments, the contrasting agent is configured to allow for detection removal of foreign matter (the projectile) from the target's body.

Figure 3:
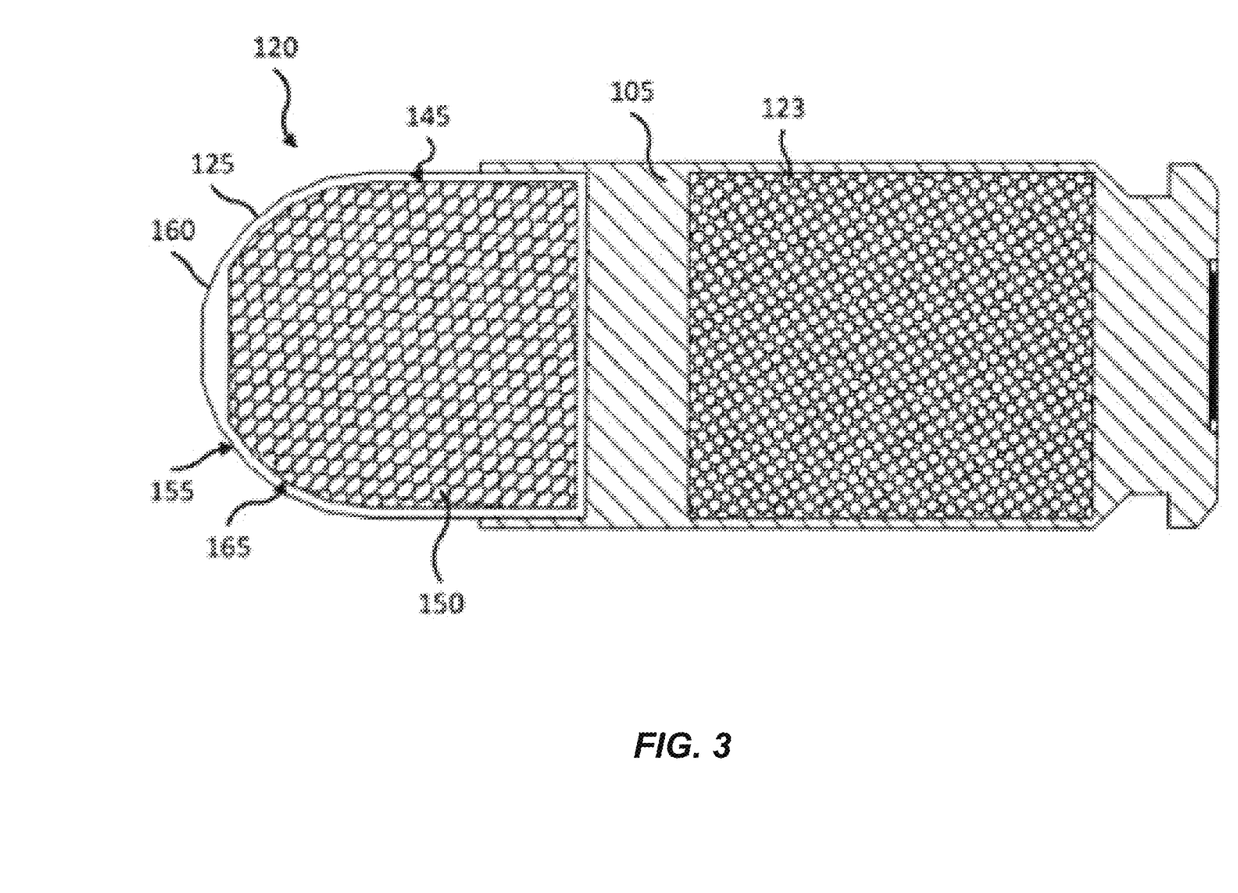
FIG. 3 is a side sectional view of an assembled small arms or firearm cartridge including a hemostatic material, according to some embodiments.

FIG. 3 illustrates a side sectional view of the cartridge 100 in an assembled state. In the illustrated embodiment, the hemostatic material 150 is illustrated as a homogeneous material throughout the interior boundary volume 145 of the projectile 120. However, this is not required. As discussed above, the projectile 120 may include more than one hemostatic material. Accordingly, in some embodiments, the hemostatic material 150 is a heterogeneous material. Further, the hemostatic material 150 may be selectively varied in density, composition, or any other characteristic.

In some embodiments, the hemostatic material 150 is further treated with one or more additional agents, such as a cauterizing agent, a paralytic agent, an anesthetic agent, and/or a sedative agent. Accordingly, the hemostatic material 150 and additional agents may be selected for any number of preferred biological responses at a delivery site. Further, the jacket 125 may include a thin film 155 on an exterior surface 160 of the jacket 125. Alternatively, or additionally, the jacket 125 may include a thin film 165 on an interior of the jacket and interfacing with the hemostatic material 150, for example, along the interior boundary volume 145. In some embodiments, the thin film 155 includes any of the aforementioned hemostatic agents. In some embodiments, the thin film 165 includes any of the aforementioned hemostatic agents. In some embodiments, the thin film 165 may protect the hemostatic material 150 from interactions with or through the jacket 125. In some embodiments, the thin film 155 and the thin film 165 are included on the jacket 125 simultaneously. In some embodiments, the thin film 155 and the thin film 165 are configured as the same hemostatic agent.

Figure 4A:
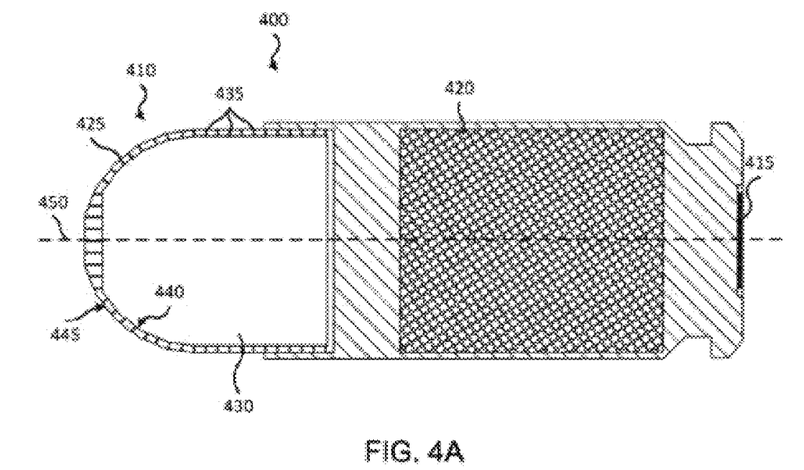
FIG. 4A is a side sectional view of a small arms or firearm cartridge having a perforated jacket, according to some embodiments.

FIG. 4A illustrates an embodiment of a small arms or firearm cartridge 400 having a shell casing 405, a projectile 410, a primer 415, and a propellant 420. The projectile 410 includes a jacket 425 and an enclosed material 430. In some embodiments, the enclosed material includes a hemostatic material, such as hemostatic material 150. The jacket 425 further includes at least one channel 435 extending from an interior surface 440 of the jacket 425 to an exterior surface 445 of the jacket 425. In the illustrated embodiment, the jacket 425 includes a plurality of channels 435, or perforations 435. The channels 435 are configured as cylindrical openings which are oriented normal to the exterior surface 445 of the jacket 425, but this is not required. For example, the channels 435 may have any desired cross section, such as ovular, hexagonal, etc., and may further have non-uniform cross sections, such as expanding between the interior surface 440 and the exterior surface 445, or transitioning from a first cross section to a second cross section. Similarly, although the channels 435 are illustrated as normal to the exterior surface 445 of the jacket 425, this is also not required. For example, the channels 435 may be oriented obliquely to the exterior surface 445, such as inclined relative to a central axis 450.

Figure 4B:
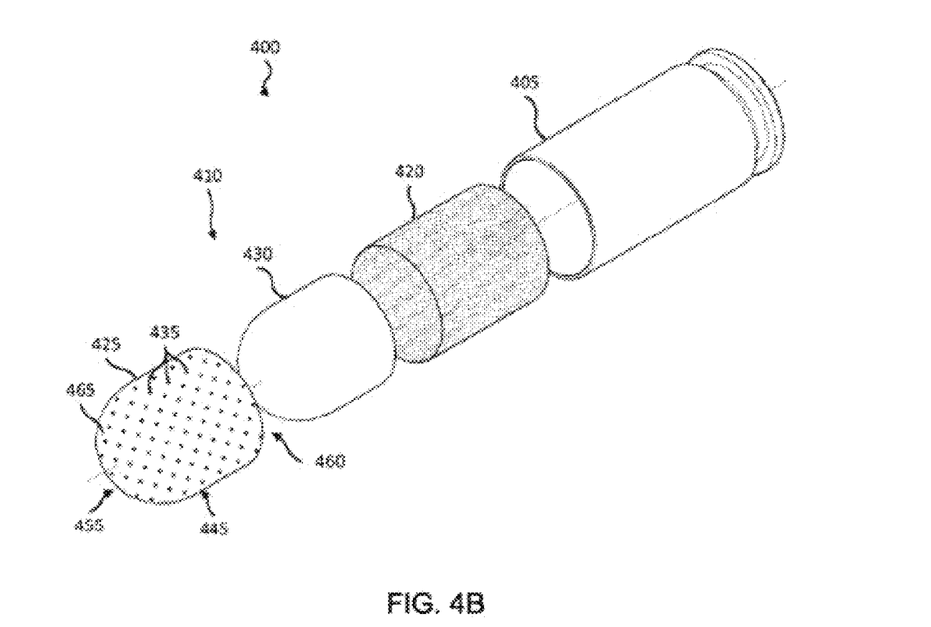
FIG. 4B is an exploded perspective view of a small arms or firearm cartridge having a perforated jacket and illustrating an external arrangement or patterning of the perforations, according to some embodiments.

FIG. 4B illustrates an exploded view of the cartridge 400. In the illustrated embodiment, the perforations 435 are uniformly distributed about the exterior surface 445 of the jacket 425, but this is not required. For example, the perforations 435 may be clustered or arranged into sectors which may overlap or be configured to cooperate with each other. Further, the perforations 435 may be arranged in a non-uniform pattern about the exterior surface 445 of the jacket 425. For example, the perforations 435 may be arranged such that the surface density of the perforations 435 is non-uniform about the exterior surface 445 of the jacket 425. For example, the density of perforations 435 may decrease from a tip portion 455 of the jacket 425 to a tail portion 460. Alternatively, or additionally, the perforations 435 may comprise a first plurality of perforations 435 and a second plurality of perforations 435 which are arranged about the exterior surface 445 of the jacket 425. The first plurality and second plurality may differ in size, shape, cross section, spatiality, obliqueness or any other characteristic. Further, the first plurality and the second plurality of perforations 435 may be disposed separately, for example, in two disparate regions. Alternatively, the first plurality and the second plurality may be interspersed, for example, in a heterogeneous arrangement about the jacket 425. For example, the heterogeneous arrangement may be configured as a uniform arrangement including the first and second pluralities of perforations 435. Alternatively, the arrangement may include a gradient of one or both of the first plurality of perforations 435 and the second plurality of perforations 435. For example, a first plurality of perforations 435 may have a consistent distribution density about the exterior surface 445 of the jacket 425, whereas the second plurality of perforations 435 has a variable distribution density about the exterior surface 445 of the jacket 425, for example, a gradient. Accordingly, one or more pluralities of perforations 435 may be arranged about the exterior surface 445 of the jacket 425 and may be configured to promote one or more of rotational stability, frangibility, expansion, distribution of hemostatic material, or any other suitable projectile characteristic. For example, the perforations 435 may be dimensioned such that hemostatic is securely retained, such as having a dimension of less than 2 mm. In other instances, the perforations 435 may be microscopic, for example, 250 µm. Accordingly, during impact at a delivery site, perforations 435 in the jacket 425 may promote delivery of the enclosed material 430.

Additionally, the jacket 425 may include a thin film 465, for example, on the exterior surface 445 of the jacket 425. The thin film 465 may be configured to protect the enclosed material 430 during storage and transport of the cartridge 400. In some embodiments, the thin film 465 is configured to break down or "cook off" during the firing or flight of the projectile 410. In other embodiments, the thin film 465 is configured as a biodegradable material. Accordingly, the thin film 465 protects the enclosed material 430 until the projectile 410 reaches the delivery site. Thus, the enclosed material 430 is in fluid communication with the surrounding tissue, either due to fracturing of the jacket 425 or through open perforations 435.

Figure 5:
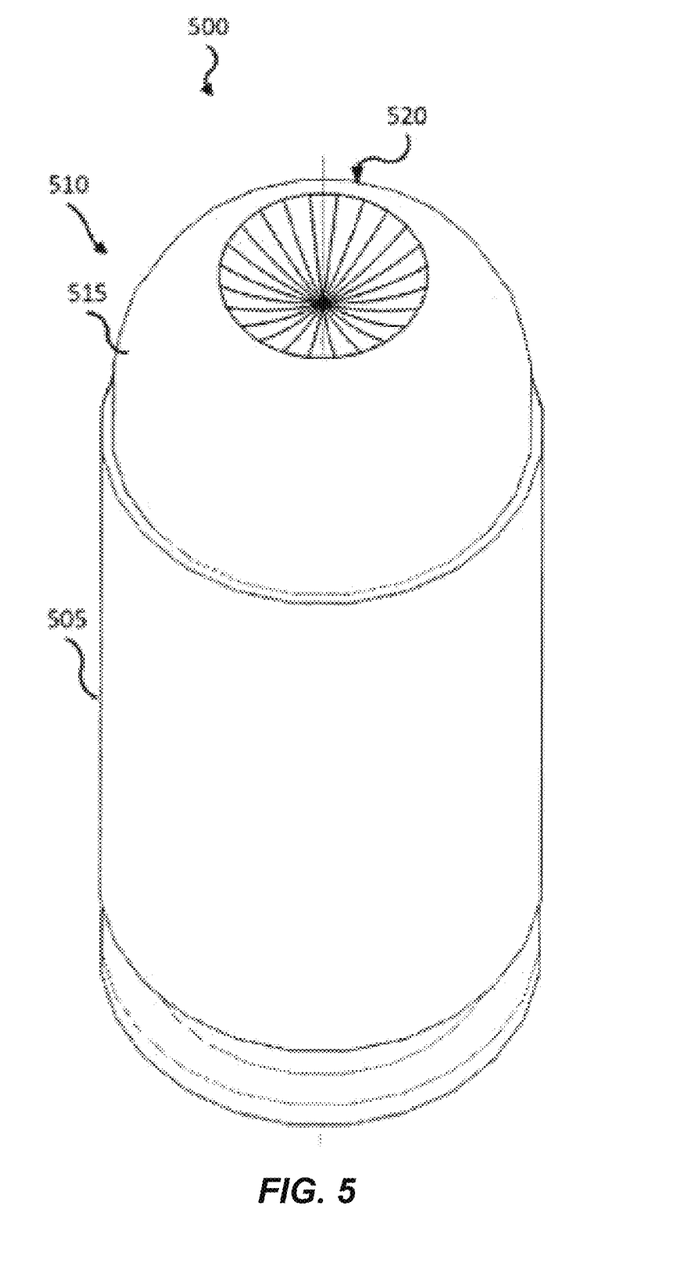
FIG. 5 is a perspective view of a small arms or firearm cartridge including a hollow point jacket, according to some embodiments.

FIG. 5 illustrates an embodiment of a small arms or firearm cartridge 500 having a shell casing 505 and a projectile 510. The projectile 510 includes a jacket 515 having a depression 520 in a tip 525 of the jacket 515. For example, the projectile 510 may be referred to as a "hollow-point" configuration. In some embodiments, the projectile further includes a tip material 530 partially within the depression 520, for example, a polymer tip. In some embodiments, projectile 510 includes an enclosed material which includes a hemostatic material, such as hemostatic material 150. In these instances, the projectile 510 includes the hemostatic material, such as hemostatic material 150, on an interior of the jacket 515. Accordingly, the depression 520 may improve delivery of the hemostatic material at a delivery site.

Figure 6:
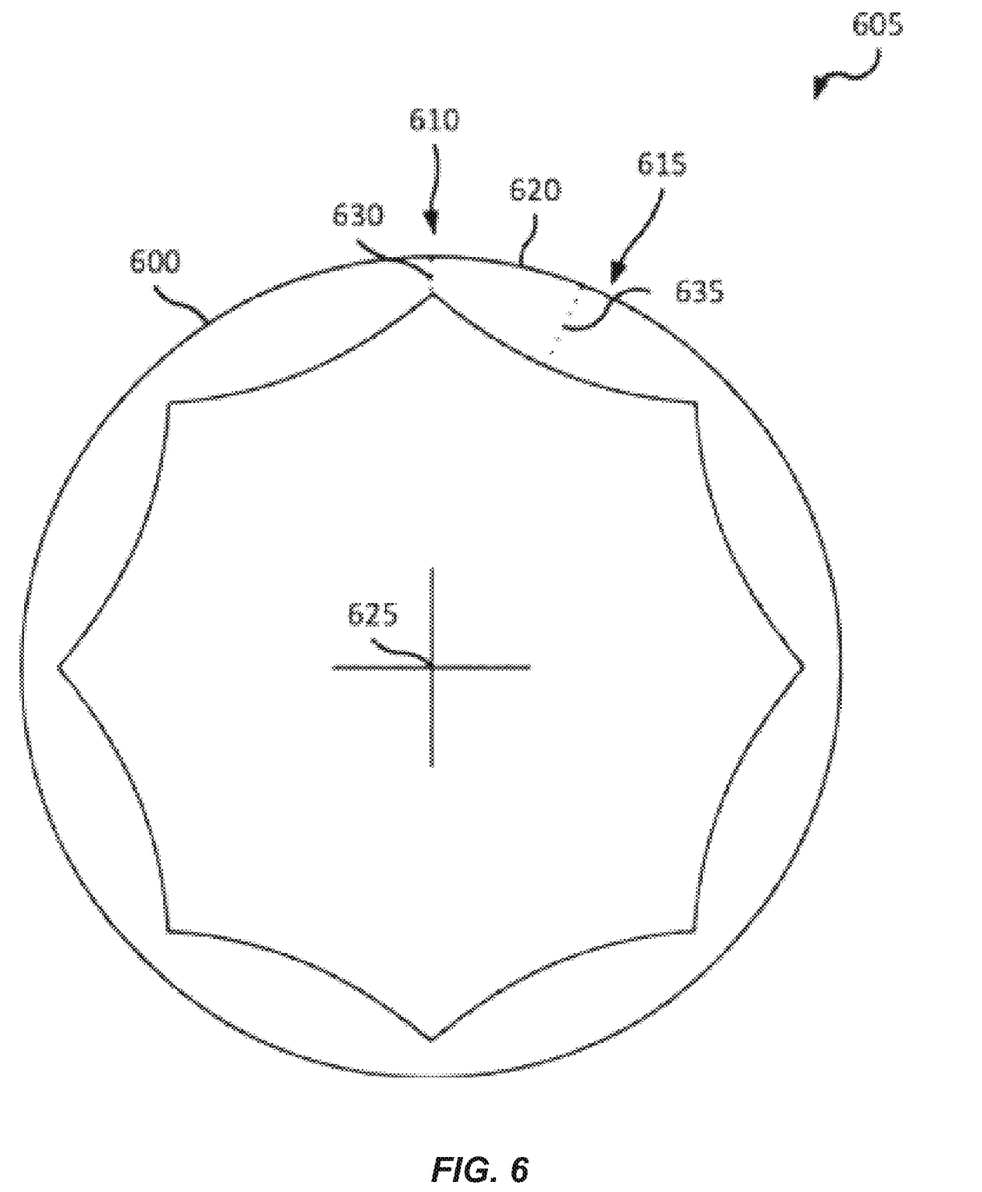
FIG. 6 is an axial sectional view of a small arms or firearm cartridge including a multiple structural regions, according to some embodiments.

FIG. 6 illustrates an axial view of a jacket 600 of a small arms or firearm projectile 605. The jacket 600 comprises a homogenous metal or alloy and includes a plurality of structural regions, including a first structural region 610 and a second structural region 615. The first structural region 610 and the second structural region 615 share an exterior surface 620 of the jacket 600, the exterior surface 620 having a constant radius about a longitudinal axis 625 of the projectile 605. The first structural region 610 has a first radial thickness 630, extending from the exterior surface 620 radially toward the longitudinal axis 625. The second structural region 615 has a second radial thickness 635, extending from the exterior surface 620 radially toward the longitudinal axis 625. In the illustrated embodiment, the first structural region 610 is weaker than the second structural region 615 due to the first radial thickness 630 being less than the second radial thickness 635. However, in other embodiments, the first structural region 610 and the second structural region 615 may comprise different alloys, having different properties, such as tensile strength or toughness. Accordingly, in these embodiments, the first structural region 610 and the second structural region 615 may have, respectively, a first radial thickness 630 and a second radial thickness 635 which are equal. However, due to the different properties of the materials in the first structural region 610 and the second structural region 615, the first structural region 610 may still be weaker than the second structural region 615. Further, the material and dimensioning of the structural regions 610, 615 may be selected based on, for example, a desired frangibility of the projectile 605. For example, large shards of the jacket 600 may inflict more immediate damage, but be easier to remove later, whereas smaller shards of the jacket 600 may inflect different effects initially, but present more difficulty in removal. Further, the material and dimensioning of the structural regions may be selected on, for example, delivery of an enclosed hemostatic material. For example, reactivity of a hemostatic material may be based, at least in part, on surface area contact with fluid at a delivery site. Accordingly, a selection of structural regions 610, 615 which provides increased surface area contact between the hemostatic material and the fluid at the delivery site may be desired.

Figure 7:
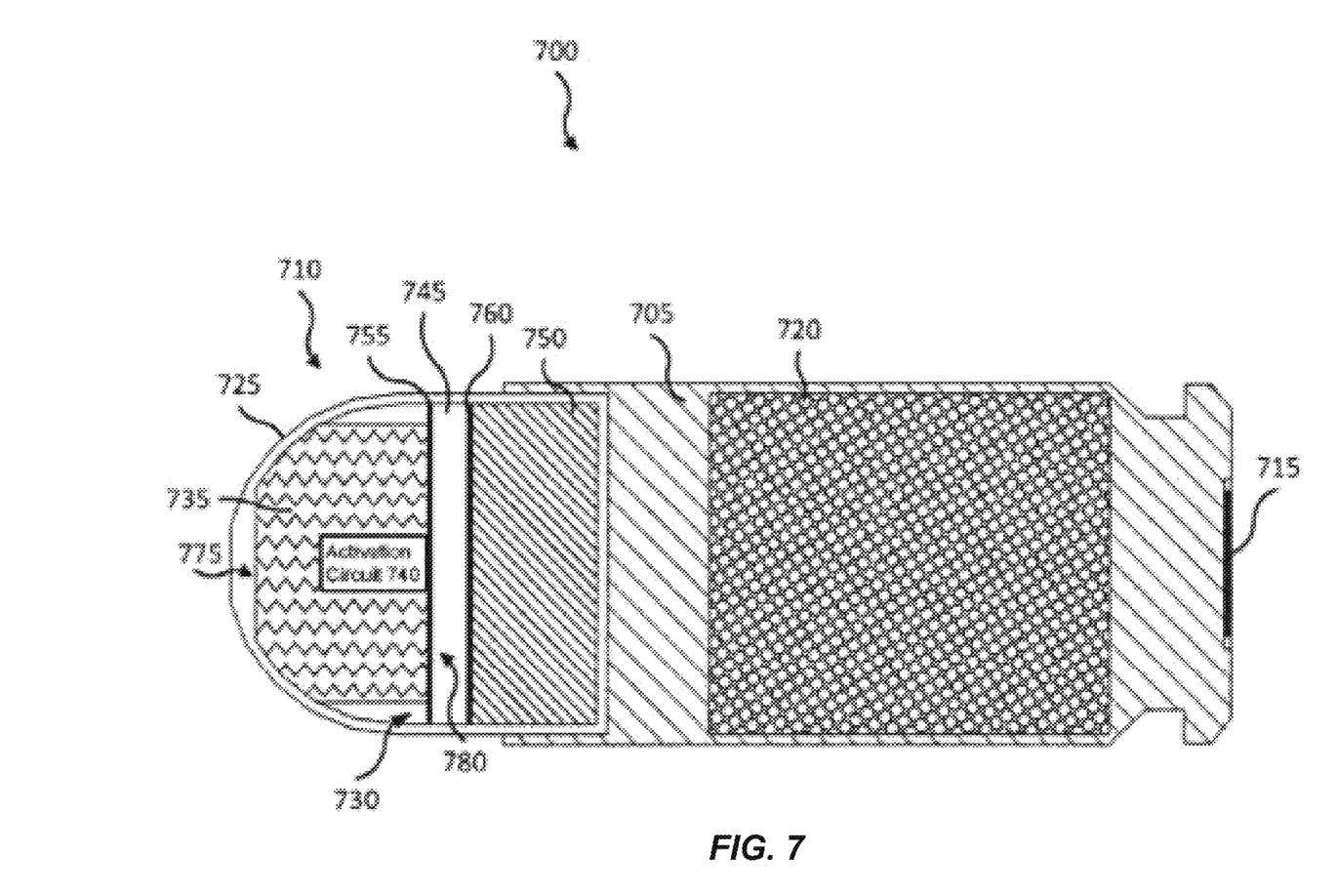
FIG. 7 is a side sectional view of a small arms or firearm cartridge including an exothermic assembly activated by a piezoelectric material, according to some embodiments.

FIG. 7 illustrates an embodiment of a small arms or firearm cartridge 700 having a shell casing 705, a projectile 710, a primer 715, and a propellant 720. The projectile 710 includes a jacket 725 and an exothermic assembly 730. In some embodiments, the exothermic assembly 730 includes a piezoelectric material 735, an activation circuit 740, an electrolytic material 745, and an exothermic material 750, however some embodiments may have more or fewer components. The components of the exothermic assembly 730 are divided by a first partition 755 and a second partition 760. The first partition 755 provides a structural platform against which the piezoelectric material 735 may be compressed. Additionally, the first partition 755, in combination with the second partition 760, retains the electrolytic material 745. The second partition 760 also retains and separates the exothermic material 750. However, in some embodiments, the exothermic material 750 and the electrolytic material 745 may be selected such that the both materials are stable at a direct contact interface. The piezoelectric material 735 and activation circuit 740 are generally located proximate a tip portion 765 of the jacket 725. Accordingly, during impact of the projectile 710, the piezoelectric material 735 is compressed, generating a voltage potential which is communicated to the electrolytic material 745. The voltage potential is communicated to the electrolytic material 745 by one or more wires 770 of the activation circuit 740. For example, the activation circuit 740 may include wires 770 coupling a crown portion 775 and a pedestal portion 780 of the piezoelectric material 735 to the electrolytic material 745. Alternatively, the activation circuit 740 may include a single wire 770 which couples either the crown portion 775 or the pedestal portion 780 to the electrolytic material 745. In this embodiment, the circuit between the piezoelectric material 735 and the electrolytic material 745 is completed by conduction through one or more of the first partition 755 and the jacket 725 itself.

Once the electrolytic material 745 is activated, for example, at impact at a delivery site, the electrolytic material 745 proceeds to activate the exothermic material 750. Accordingly, the temperature of the jacket 725 and surrounding area rapidly increases, cauterizing nearby tissue and thereby staunching fluid flow. Additionally, in further embodiments, the exothermic material 750 may be configured to cooperate with an additional material, such as a hemostatic agent. For example, certain procoagulant supplementors have a known exothermic effect. Accordingly, the projectile 710 may further include a hemostatic agent, wherein the hemostatic agent and exothermic material 750 are configured for cooperative application. In some embodiments, the hemostatic material may be retained with the exothermic material 750. In other embodiments, the hemostatic material is retained separately, for example, by a third partition (not shown).

The activation circuitry 740 may further include additional components, such as semiconductor gates, switches, transformers, processors, transceivers, and the like. For example, the activation circuit 740 may include a transformer which steps the voltage generated by the piezoelectric material 735 up or down in accordance with a characteristic of the electrolytic material 745. Alternatively, or in addition, the activation circuitry 740 may include transceiver circuitry which is configured to enable or "arm" the projectile 705. Accordingly, accidental activations of the exothermic material 750 may be reduced. Alternatively, or in addition, the activation circuitry 740 may include one or more thermoreactive elements. For example, the projectile 705 may be armed in response to a rapid increase in temperature during firing.

Figure 8:
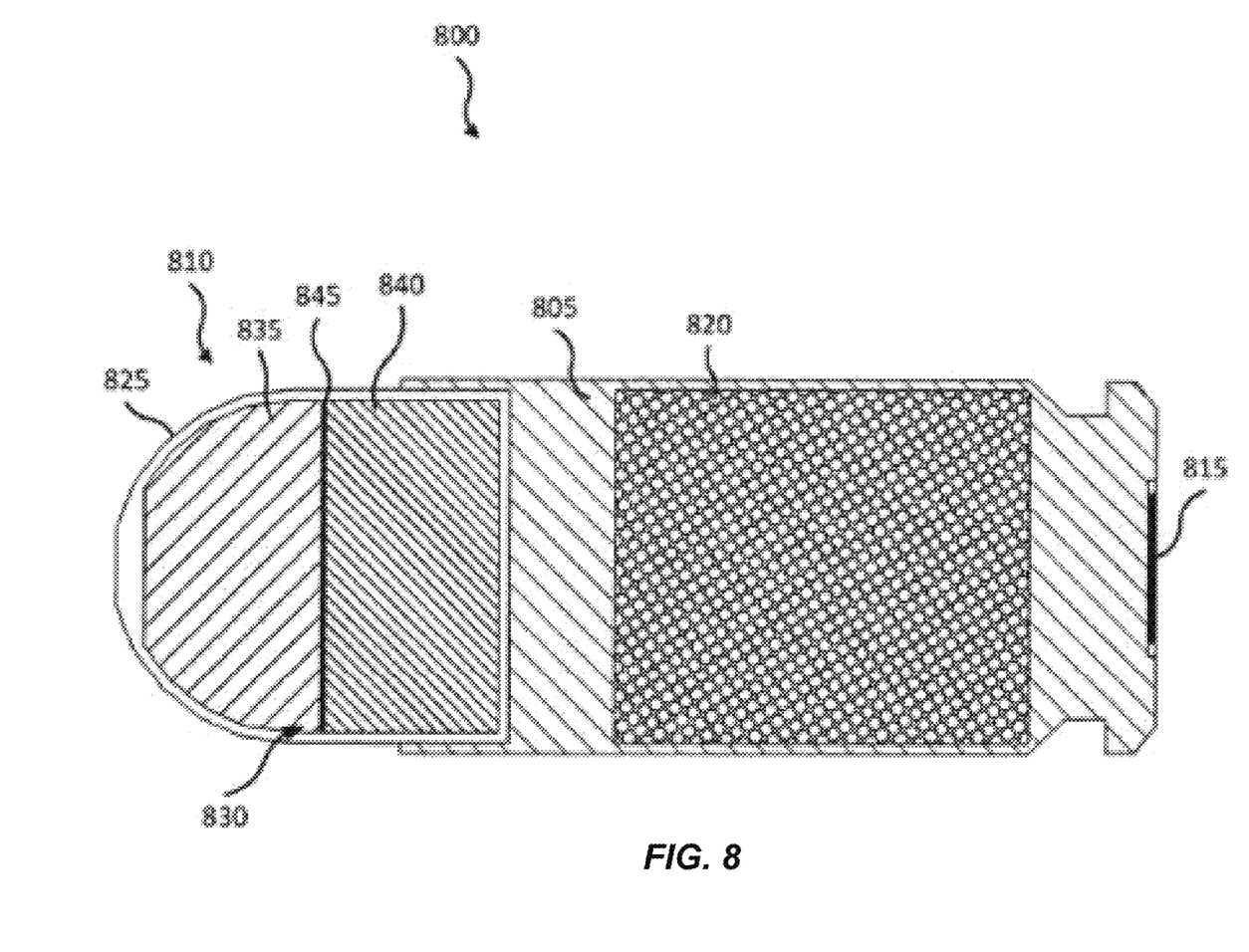
FIG. 8 is a side sectional view of a small arms or firearm cartridge two materials separated by a partition, according to some embodiments.

FIG. 8 illustrates an embodiment of a small arms or firearm cartridge 800 having a shell casing 805, a projectile 810, a primer 815, and a propellant 820. The projectile 810 includes a jacket 825 and a partitioned assembly 830. The partitioned assembly 830 includes a first material 835 and a second material 840 which are separated from each other by a partition 845. In some embodiments, the first material 835 and the second material 840 are configured as binary agents for an exothermic reaction. Further, in some embodiments, the partition 845 is configured to break down during one or both of firing and flight of the projectile 810. Accordingly, as the partition 845 breaks down, the first material 835 and the second material 840 react, increasing the surface temperature of the jacket 825. During impact and penetration at the delivery site, the heat from the jacket 825 may cauterize surrounding tissue and decrease a likelihood of exsanguination. Alternatively, the partition 845 may be configured to persist through firing and flight of the projectile 710. In these embodiments, the jacket 725 may be configured, such as with a plurality of structural regions, to break apart such that the first material 835 and the second material 840 react upon impact at the delivery site. By way of additional example, the first material 835 and the second material 840 may include hemostatic materials. In these embodiments, two hemostatic materials may be retained within the jacket 825 regardless of their joint chemical stability. Further, the first material 835 and the second material 840 may be configured as binary agents of a single hemostatic material. Accordingly, the shelf life of the hemostatic material may be improved.

Figure 9:
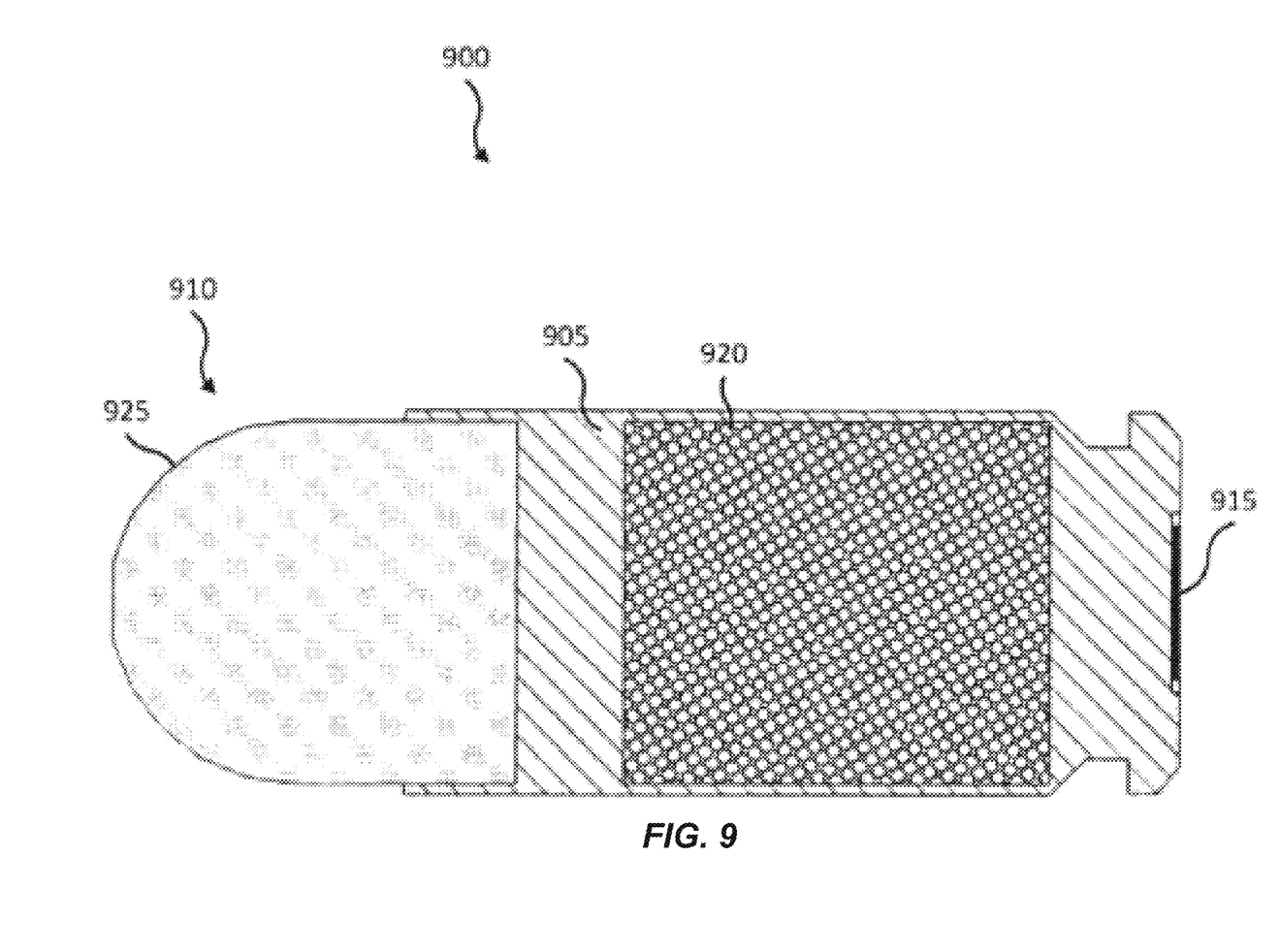
FIG. 9 is a side sectional view of a small arms or firearm cartridge including a jacket and hemostatic compound formed as a unitary body, according to some embodiments.

FIG. 9 illustrates an embodiment of a small arms or firearm cartridge 900 having a shell casing 905, a projectile 910, a primer 915, and a propellant 920. The projectile 910 comprises a unitary body 925. Whereas other embodiments include a jacket surrounding a hemostatic material, the unitary body 925 includes hemostatic material integrally distributed within. In some embodiments, the unitary body 925 includes a plurality of hemostatic granules, a plurality of ballast granules, and a binding agent. The ballast granules, such as metals or other dense materials, may improve ballistic properties of projectile 910. In some embodiments, the ballast granules may include a second plurality of dense hemostatic granules. The binding agent forms a solid composite material integral with the hemostatic granules and the ballast granules. The ballast may be selected such that it readily decomposes in the presence of fluid at the delivery site. Accordingly, the hemostatic granules may be readily distributed after impact.

Figure 10:
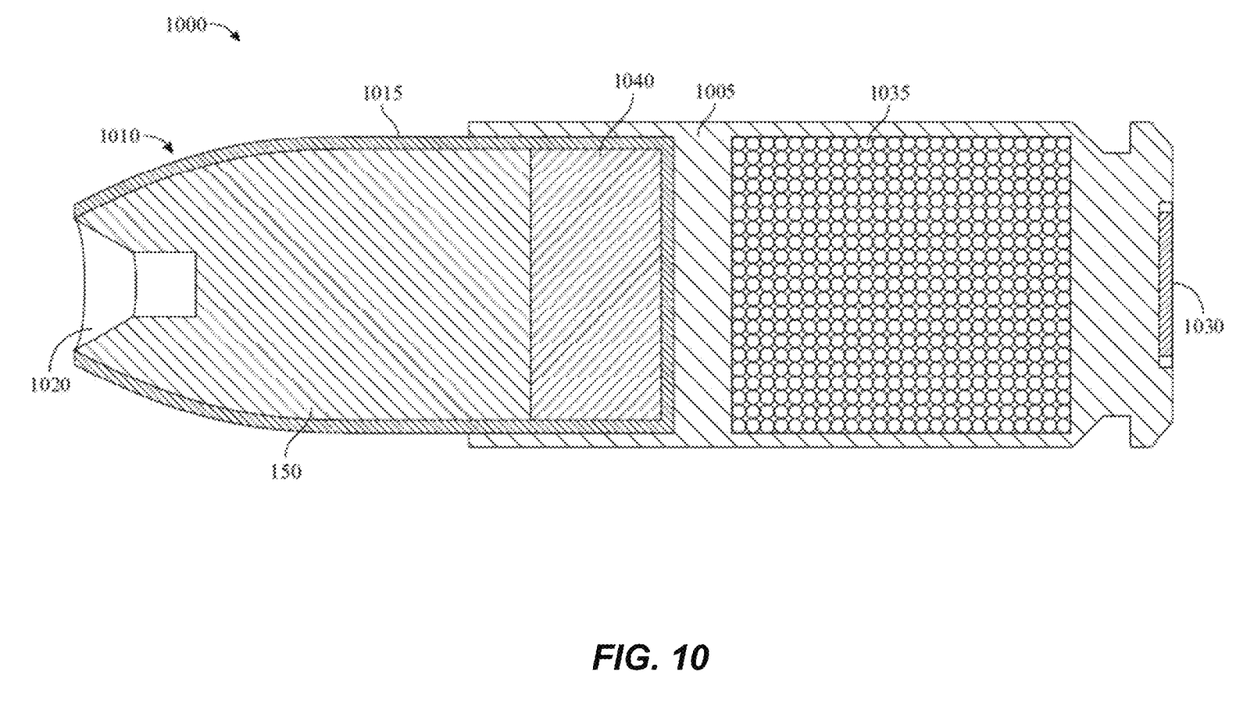
FIG. 10 is a side sectional view of a small arms or firearm cartridge including a jacket, a hemostatic compound, and a weighted pellet, according to some embodiments.

FIG. 10 illustrates an embodiment of a small arms or firearm cartridge 1000 having a shell casing 1005 and a projectile 1010. The projectile 1010 includes a jacket 1015 having a depression 1020 in a tip 1025 of the jacket 1015. For example, the projectile 1010 may be referred to as another embodiment of the "hollow-point" configuration. In some embodiments, the projectile 1010 includes an enclosed material which includes a hemostatic material, such as hemostatic material 150. In these instances, the projectile 1010 includes the hemostatic material, such as hemostatic material 150, on an interior of the jacket 1015. Accordingly, the depression 1020 may improve delivery of the hemostatic material at a delivery site. The projectile may further include a primer 1030 and a propellant 1035. The projectile may further include a weighted pellet 1040. The weighted pellet 1040 may be made of lead. In some embodiments, the weighted pellet 1040 is bonded to the jacket 1015. In some embodiments, the weighted pellet 1040 is bonded to the jacket 1015 through diffusion bonding. In some embodiments, the weighted pellet 1040 is bonded to the jacket 1015 using Corbin Core Bond™. In some embodiments, the weighted pellet 1040 is bonded to or coated with a contrasting agent.

In some embodiments, there is a delay between impact and the activation or release of the hemostatic material 150. This is because gun users are relying on the time between the bullet strike and incapacitation (where the threat no longer has potential to be harmful) to be as quick as possible. However, by releasing or activating the hemostatic agent after a delay, the time between the incapacitation and death need to be extended when considering preservation of life and intelligence in a mission.

Thus, the disclosure provides, among other things, a delivery vehicle of a plurality of biocompatible trauma-mitigating agents, as well as combinations which provide a more holistic less-than-lethal delivery system. Various features and advantages of the disclosure are set forth in the following claims.

What is claimed is:

1. A firearm projectile, comprising:
   a shell, having an interior and an exterior; and
   a hemostatic material retained in the interior of the shell;
   wherein the hemostatic material has a mechanical modulus above 25,000 Pa; and
   wherein the shell has a front and a back, and the shell further comprises a weighted pellet bonded to the back of the shell.

2. The firearm projectile of claim 1, wherein the shell comprises a plurality of perforations, and wherein the plurality of perforations are configured to provide, upon an impact of the projectile, fluid communication between the hemostatic material and the exterior of the shell via the plurality of perforations.

3. The firearm projectile of claim 1, wherein the hemostatic material comprises a polymer core configured to provide a scaffold for inducing hemostasis in a local wound volume.

4. The firearm projectile of claim 1, further comprising a contrasting agent.

5. The firearm projectile of claim 1, further comprising: a lubricating agent retained in the interior of the shell.

6. The firearm projectile of claim 1, further comprising: 0.5 to 3 grains of Kaolin retained in the interior of the shell.

7. The firearm projectile of claim 1, wherein the hemostatic material is comprised of a plurality of expandable polymer pellets.

8. The firearm projectile of claim 1, further comprising a disinfecting agent retained in the interior of the shell.

9. The firearm projectile of claim 1, having a jacket with a thickness between 0.01 inches and 0.015 inches and wherein the length of the projectile is between 0.6 inches and 0.75 inches.

10. A firearm cartridge, comprising:
    a cartridge case having an open end, a closed end, and a longitudinal axis;
    a shell, having an interior and an exterior, the shell configured for secure retention in the open end of the cartridge case,
    a propellant retained within the cartridge case between the shell and the closed end of the cartridge case;
    an enclosed material retained in the interior of the shell;
    wherein the enclosed material is configured as a hemostatic material; and
    wherein the hemostatic material has a mechanical modulus above 25,000 Pa; and
    wherein the shell has a front and a back, wherein the shell further comprises a weighted pellet bonded to the back of the shell.

11. The firearm cartridge of claim 10, wherein the shell includes a plurality of perforations, and wherein the plurality of perforations are configured to provide, upon an impact of the cartridge, fluid communication between the hemostatic material and the exterior of the shell via the plurality of perforations.

12. The firearm cartridge of claim 10, wherein the hemostatic material comprises a polymer core configured to provide a scaffold for inducing hemostasis in a local wound volume.

13. The firearm cartridge of claim 10, further comprising: a contrasting agent.

14. The firearm cartridge of claim 10, further comprising: a lubricating agent retained in the interior of the shell.

15. The firearm cartridge of claim 10, further comprising: 0.5 to 3 grains of Kaolin retained in the interior of the shell.

16. The firearm cartridge of claim 10, wherein the hemostatic material is comprised of a plurality of expandable polymer pellets.

17. The firearm cartridge of claim 10, further comprising: a disinfecting agent retained in the interior of the shell.

18. The firearm cartridge of claim 10, having a jacket with a thickness between 0.01 inches and 0.015 inches a length between 0.6 inches and 0.75 inches.

* * * * *